US00PP11838P2

(12) United States Plant Patent
Zary

(10) Patent No.: US PP11,838 P2
(45) Date of Patent: Apr. 24, 2001

(54) HYBRID TEA ROSE PLANT NAMED 'JACBITOU'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/267,561

(22) Filed: Mar. 12, 1999

(51) Int. Cl.[7] ..... A01H 5/00
(52) U.S. Cl. ..... Plt./132
(58) Field of Search ..... Plt./130, 132

*Primary Examiner*—Howard J. Locker
(74) *Attorney, Agent, or Firm*—Klarquist Sparkman Campbell Leigh & Whinston, LLP

(57) ABSTRACT

A hybrid tea rose plant having dark green, glossy disease-resistant foliage on a vigorous, upright but compact plant having large, yellow and pink blend fragrant flowers.

1 Drawing Sheet

1

The present invention relates to a new and distinct variety of rose plant of the hybrid tea class which was originated by me by crossing the variety 'JACtou', U.S. Plant Pat. No. 8,706, with the variety 'KEIbian', U.S. Plant Pat. No. 8,476.

The primary objective of this breeding was to produce a new rose variety having the dark green, glossy, disease-resistant foliage, fragrance and thick petals of the female parent combined with the fragrance, dark foliage and vigor of the male parent. It was also hoped to deepen the color of the flowers by using the deep yellow flowered male parent. The objective was substantially achieved, along with other desirable improvements, as evidenced by the following unique combination of characteristics that are outstanding in the new variety and that distinguish it from its parents, as well as from all other varieties of which I am aware:

1. Vigorous, upright but quite compact growth.
2. Dark green, glossy foliage.
3. Fragrant flowers.
4. Large yellow and pink blend flowers.
5. Disease resistant foliage.

'JACbitou' is a yellow and pink blend garden rose. This hybrid tea is a compact plant growing to 4½ feet in Somis, Calif., unlike most hybrid teas that grow to 5½ feet. Its stems are strong but only 14 to 16 inches long. Flowers are large and quite fragrant and presented one to a stem.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACtou', U.S. Plant Pat. No. 8,706
*Pollen parent.*—*'KEIbian'*, U.S. Plant Pat. No. 8,476

2

Classification:

*Botanical.*—*Rosa hybrida.*
*Commercial.*—Hybrid Tea.

FLOWER

Observations made from specimens grown in a garden environment at Somis, Calif., in March 1997 to December 1998.

Blooming habit: Recurrent.

Bud:

*Size.*—About 1¾ inches long when the petals start to unfurl.

*Form.*—The bud form is long, pointed ovoid.

*Color.*—When sepals first divide, bud color is Yellow Group 11D except where the petal has been exposed to the sun. In exposed areas it is Red Group 45B to Red Group 45C. When half blown, the upper sides of the petals are on the outermost petals Red Group 45A on the edges changing to Red Group 45B then Red Group 45C on the outer ⅓ of the petal. The inner ⅔'s are Yellow Group 11D. The inner petals are Yellow Group 11D. The lower sides of the petals are Yellow Group 11D with only a slight edge of Red Group 45D on the outer tip of the petals. The outermost guard petals have considerably more Red Group 45B, Red Group 45C, and Red Group 45D that they acquire from exposure to the sun in the bud stage.

*Sepals.*—Color: Green Group 138B except when exposed to bright sunlight, they acquire some Greyed-Purple Group 183D. Surface texture: Covered in fine hairs. There are three lightly to normally appendaged sepals. There are two unappendaged sepals with hairy edges.

*Receptacle.*—Color: Yellow-Green Group 146A with Greyed-Purple Group 183D on areas exposed to bright sun. Shape: Funnel. Size: Medium, about 7/16×⅜ inch. Surface: Smooth.

*Peduncle.*—Length: Short, averaging about 2½ inches. Surface: Glandular. Color: Yellow-Green Group 146C with reddish glands close to Greyed-Red Group 183C. The peduncle can also have some color from sun exposure close to Greyed-Red Group 183D. Strength: Stiff, erect.

Bloom:

*Size.*—Large. Average open size is five inches.

*Borne.*—Singly.

*Stems.*—Strength: Strong. Average length is about 14 to 16 inches.

*Form.*—When first open: High-centered. Permanence: Retains its form to the end, outer petals curl back.

*Petalage.*—Number of petals under normal conditions: 35.

*Color.*—The upper sides of the petals are Yellow Group 11D on the inner petals. The outer petals are Red Group 45A on the edges changing to Red Group 45B then Red Group 45C on the outer one-third of the petal. The inner ⅔'s of the petal are Yellow Group 11D. The reverse sides of the petals are Yellow Group 11D with only a slight edge of Red Group 45D on the outer tips of the petals. The outermost petals have considerably more Red Group 45B, Red Group 45C, and Red Group 45D that they acquired from exposure to the sun in the bud stage. The base of each petal has on the upper surface a small 1/16×1/16 inch Yellow Group 11B color spot. The lower surface has a large (⅖×⅖ inch) Yellow-Orange Group 15C color spot. The major color on the upper side is Yellow Group 11D.

*Variegations.*—None.

*Discoloration.*—The general tonality at the end of the first day: No change. At the end of the third day: As the flower opens, the outermost petals acquire Red Group 45B, Red Group 45C and Red Group 45D on the edges.

*Fragrance.*—Moderate, damask.

Petals:

*Texture.*—Thick.

*Shape.*—Round to deltoid.

*Form.*—Tips slightly recurved.

*Arrangement.*—Imbricated. Petaloids in the center are few, small, Yellow Group 11C and range from ¼ to ½ inch long and from 3/17 to 5/16 inch wide.

*Persistence.*—Petals drop off cleanly before drying.

*Lastingness.*—On the plant: Fair (about five to six days). As a cut flower: Fair (about seven to eight days).

Reproductive parts:

*Anthers.*—Size: Medium. Quantity: Many. Color: Yellow-Orange Group 16C. Arrangement: Regular around styles.

*Filaments.*—Color: Yellow-Orange Group 23C.

*Pollen.*—Present.

*Styles.*—Color: Orange-White Group 159C.

*Stigmas.*—Color: Orange-White Group 159D.

Plant:

*Form.*—Bush.

*Growth.*—Vigorous, upright, branching. At maturity, height is 4 to 4½ feet, width is 3 to 3½ feet.

Foliage: Number of leaflets on normal mid-stem leaves: Seven or five.

*Size.*—Large (about 6½ inches long×5 inches wide).

*Quantity.*—Abundant.

*Color.*—New foliage: Upper and lower surfaces: Greyed Orange Group 176A. Old foliage: Upper surface: Green Group 139A. Lower surface: Green Group 138B.

Leaflets:

*Shape.*—Oval.

*Texture.*—Leathery, glossy.

*Edge.*—Serrated.

*Serration.*—Single, small.

*Petiole rachis.*—Color: Green Group 138B.

*Petiole underside.*—Smooth, with occasional prickles.

*Stipules.*—Long, smooth (about 1 inch bearded).

*Disease resistance.*—Mildew and rust resistant, black-spot susceptible under normal growing conditions.

Wood:

*New wood.*—Color: Yellow-Green Group 147C. Bark: Smooth.

*Old wood.*—Color: Green Group 137C. Bark: Smooth.

Prickles:

*Quantity.*—On main canes from base: Ordinary. On laterals from main canes: Ordinary.

*Form.*—Medium, hooked downward.

*Color when young.*—Greyed-Orange Group 175C.

*Color when mature.*—Greyed Orange Group 173D.

Small prickles:

*Quantity.*—On main stalks: None. On laterals: None.

I claim:

1. A new and distinct variety of rose plant of the hybrid tea class, substantially as herein shown and described, characterized particularly by dark green, glossy disease-resistant foliage on a vigorous, upright but compact plant having large, yellow and pink blend fragrant flowers.

* * * * *

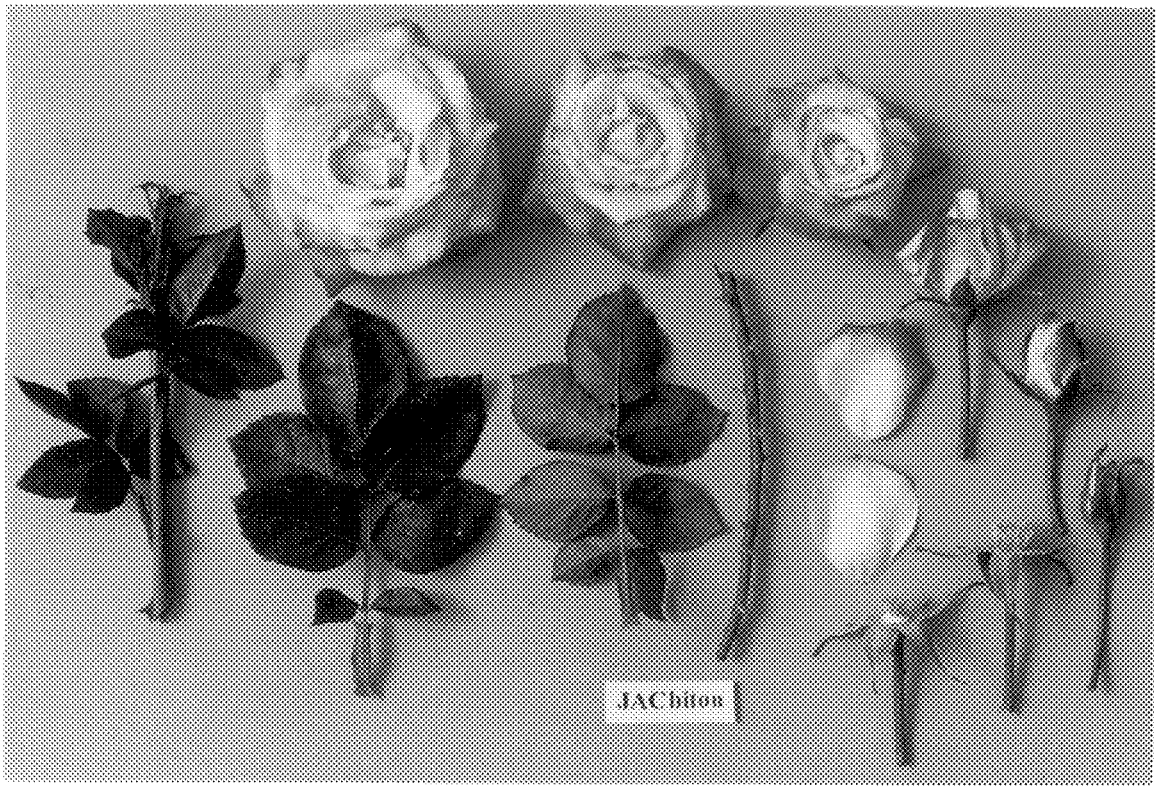
JAC bilton